(12) United States Patent  
Muzzammel

(10) Patent No.: US 6,641,581 B2
(45) Date of Patent: Nov. 4, 2003

(54) VARIABLE ANGLE CERVICAL EXCISION ELECTRODE

(76) Inventor: Mohiuddin M. Muzzammel, 11323 Bright Pond La., Reston, VA (US) 20194

( * ) Notice: Subject to any disclaimer, the term of this patent is extended or adjusted under 35 U.S.C. 154(b) by 0 days.

(21) Appl. No.: 10/262,938

(22) Filed: Oct. 3, 2002

(65) Prior Publication Data

US 2003/0109873 A1 Jun. 12, 2003

Related U.S. Application Data

(63) Continuation-in-part of application No. 10/011,297, filed on Dec. 11, 2001, now abandoned.

(51) Int. Cl.⁷ .............................................. A61B 18/14
(52) U.S. Cl. ........................................... 606/45; 606/41
(58) Field of Search ............................... 606/41, 42, 43, 606/44, 45, 46, 47, 48, 49, 50

(56) References Cited

U.S. PATENT DOCUMENTS

| 5,032,124 | A | | 7/1991 | Menton ........................ 606/19 |
|---|---|---|---|---|
| 5,415,656 | A | * | 5/1995 | Tihon et al. ................... 606/46 |
| 5,505,728 | A | * | 4/1996 | Ellman et al. ................. 606/39 |
| 5,527,331 | A | * | 6/1996 | Kresch et al. ............... 606/170 |
| 5,554,159 | A | | 9/1996 | Fischer ......................... 606/45 |
| 5,676,663 | A | | 10/1997 | Kim .............................. 606/45 |
| 5,683,387 | A | * | 11/1997 | Garito et al. .................. 606/45 |
| 5,951,550 | A | | 9/1999 | Shirley et al. ................. 606/45 |
| 6,068,628 | A | * | 5/2000 | Fanton et al. ................. 606/41 |
| 6,267,759 | B1 | * | 7/2001 | Quick .......................... 606/47 |
| 6,416,513 | B1 | * | 7/2002 | Dresden ....................... 606/45 |
| 2001/0014779 | A1 | * | 8/2001 | Burbank et al. ............ 600/564 |
| 2002/0049441 | A1 | * | 4/2002 | George et al. ................ 606/47 |

\* cited by examiner

*Primary Examiner*—Michael Peffley
*Assistant Examiner*—Aaron Roane
(74) *Attorney, Agent, or Firm*—Patent & Trademark Services; Thomas Zack; Joseph H. McGlynn

(57) ABSTRACT

An electrode for the excision of tissue from the cervix. The electrode, at one end, has a fine wire which can be rotated 360 degrees and which can be varied depending on the size of the cervix and the size of the lesion. This enables a single instrument to remove lesions, instead of using different sized instruments.

9 Claims, 6 Drawing Sheets

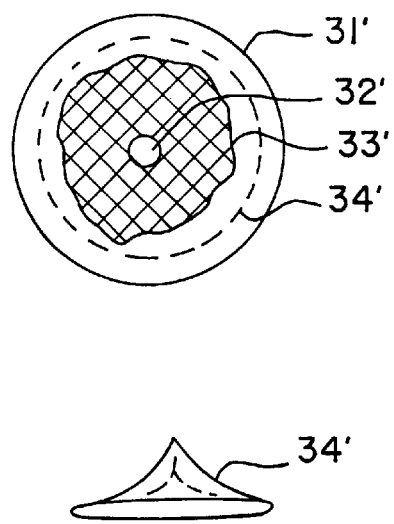
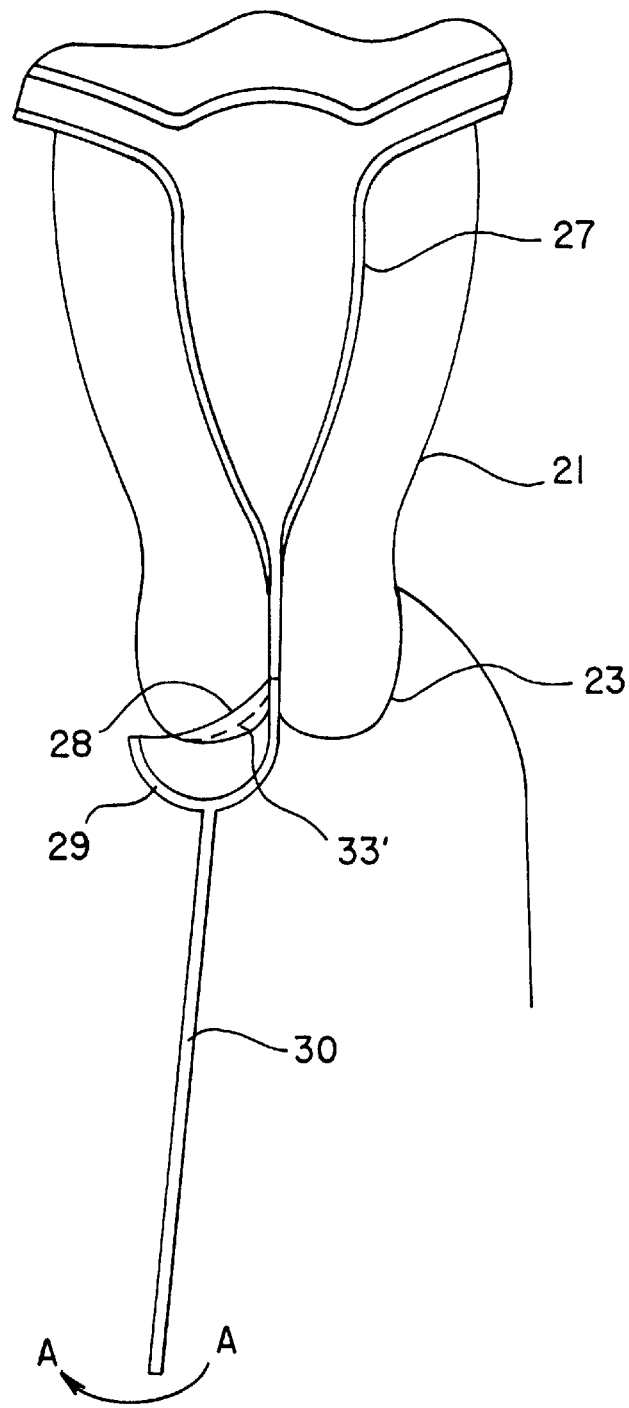
FIG.5A
FIG.5B
FIG.5C

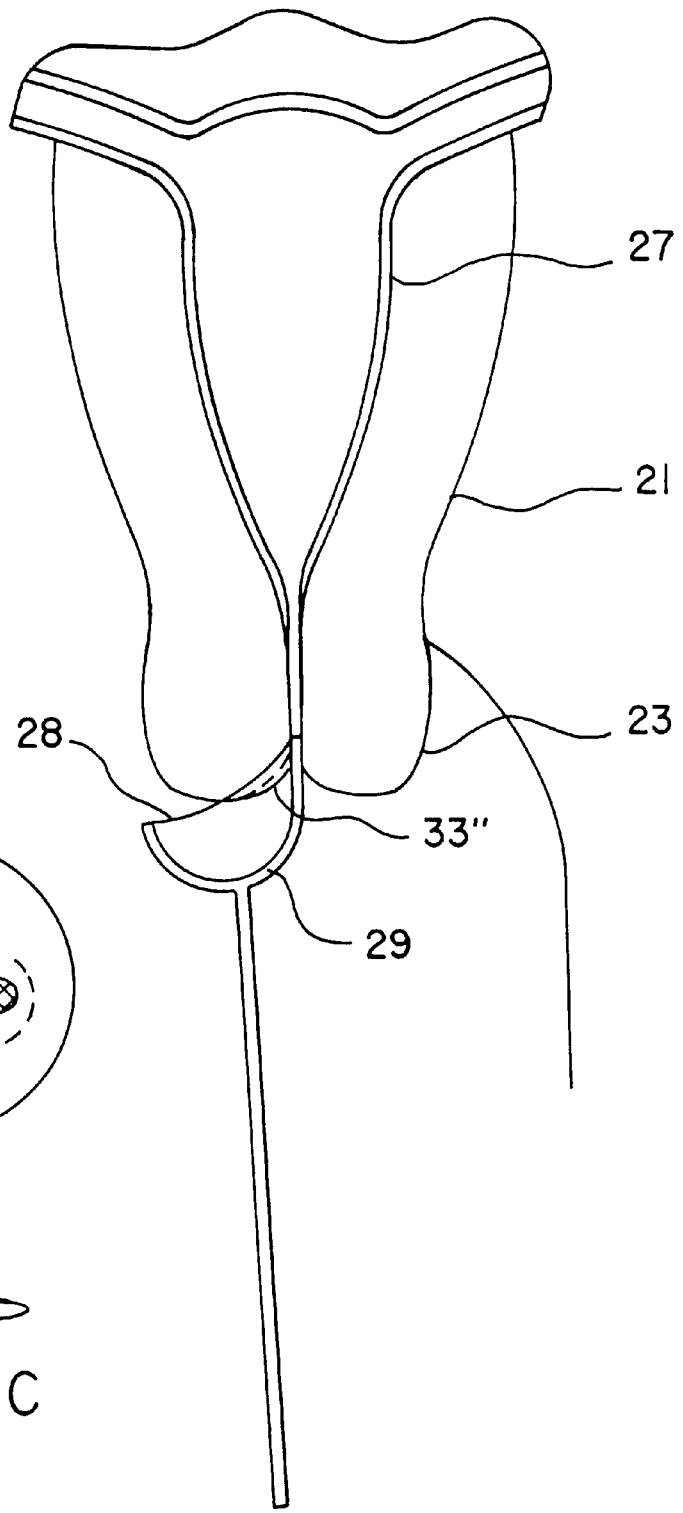

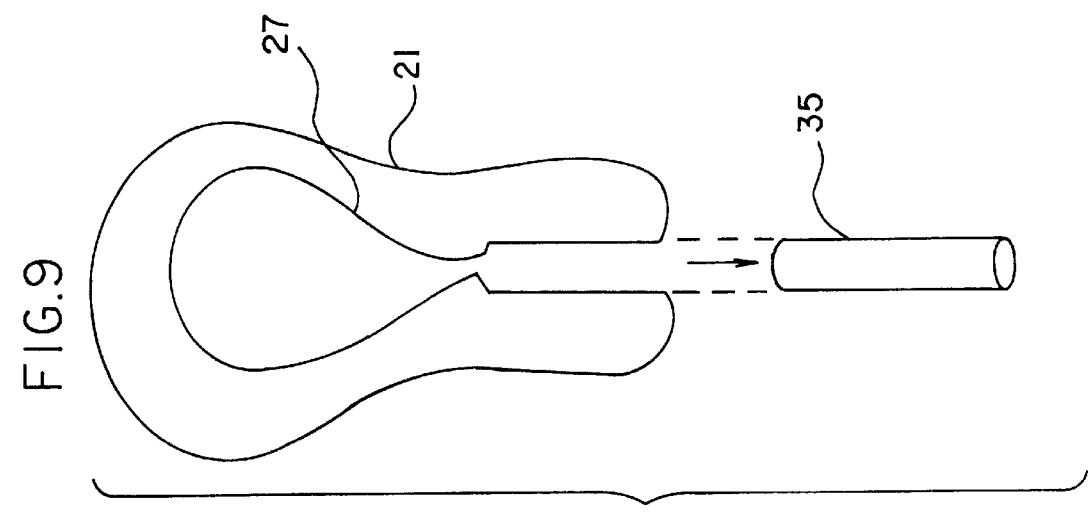
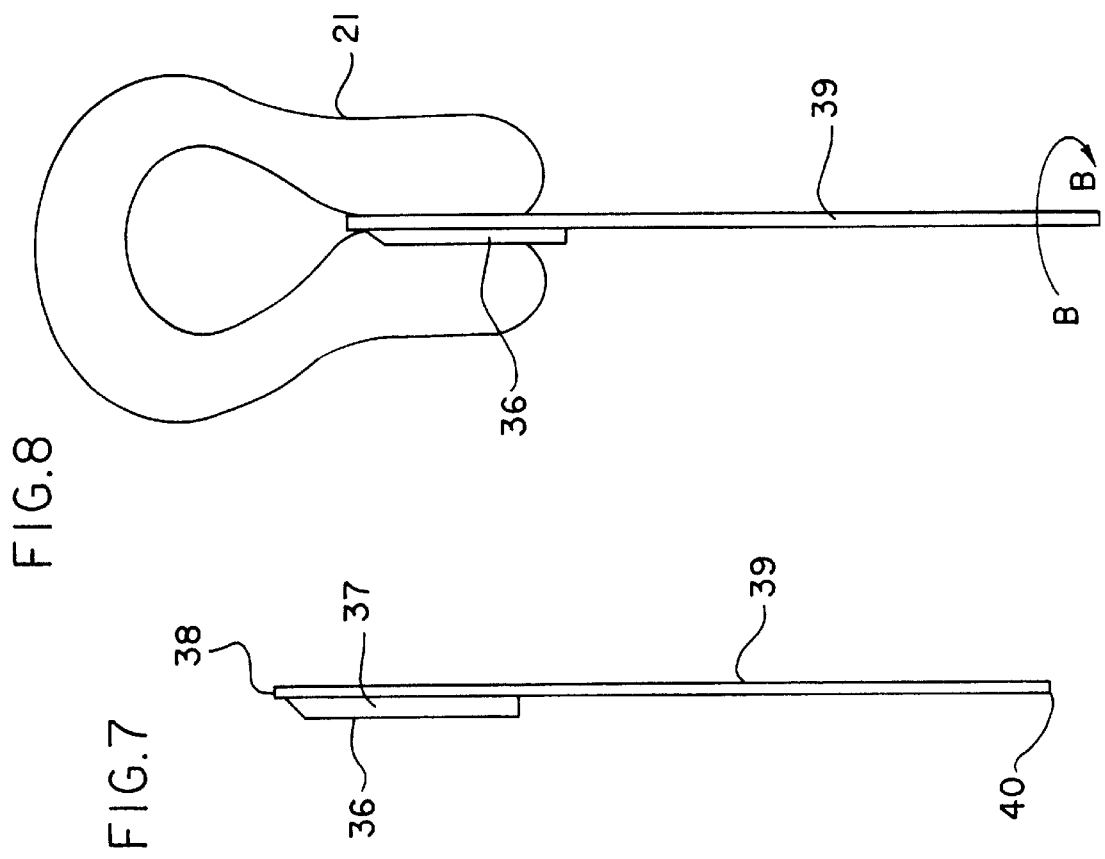

VARIABLE ANGLE CERVICAL EXCISION ELECTRODE

This application is a Continuation-in-Part of Ser. No. 10/011,297, filed Dec. 11, 2001, now abandoned.

BACKGROUND OF THE INVENTION

This invention relates in general to an electrode and in particular to an electrode used for excision of suspected abnormal human tissue.

Using electrodes to remove tissue from a human or other animal are known. A laser beam may be used in this process. When using such a beam, a guiding tubular structure can be employed to direct the beam to the desired location where it may be deflected by a deflection member. This action can allow the laser beam to sweep in a conical configuration. Another electro-surgical instrument used for excision of a tissue finds particular use in the transformation zone of the uterine cervix. In that particular instrument a stop arm is used.

Still another type of related instrument is referred to as a cone biopsy instrument and has a cuff of electrical insulating material, a core positioned within the cuff having an electrical conductor, a wire carrier of electrical insulating material with projecting arms, an electrically conducting wire connected between a wire carrier arm and the core, an implant sleeve freely rotating on the swaged portion of the core between the wire carrier and tip, and a cervical guide tip of electrical insulating material carried on the core. Another type of instrument is entitled an endocervical conization electrode apparatus. This instrument is used for excising a tissue specimen from a uterine cervix having a substantially constant section. In that instrument an electrode is used for excising tissue and has an extension member.

Still another common type of electrode currently being used to remote tissue is the loop electrode excision procedure (LEEP). With the LEEP, loops of various shapes and sizes, at least nine, are used. These loops may be different sizes and semicircular in shape with different radiuses, or the loops may be rectangular in shape and different sizes. Specific sizes and shapes are employed depending on the depth of the tissue to be removed and the width of the removed tissue. The size and location of the tissue to be removed and the size of the patient's cervix are also factors considered in selecting the particular loop used in the LEEP.

In the present invention, one instrument is used to replace the many different sizes and shapes of loops used in the LEEP for excision of tissue with various widths and depths of abnormalities.

DESCRIPTION OF THE PRIOR ART

Using electrodes for excising tissue from a human or other animal is known in the prior art. For example, U.S. Pat. No. 5,032,124 to Menton discloses an electrode for excising tissue which has a hollow tube through which a laser beam can be passed.

U.S. Pat. No. 5,554,159 to Fischer discloses an electrode for excising tissue which has a stop arm which is positioned at a right angle to the electrode.

U.S. Pat. No. 5,676,663 to Kim discloses an electrode for excising tissue which has a plurality of radially projecting arms.

U.S. Pat. No. 5,951,550 to Shirley et al. discloses an electrode for excising tissue which has an extension member extending radially from the electrode.

The present invention is directed to an electrode for excision of tissue from the cervix and which can be rotated 360 degrees at one end, all as will be detailed in the specification that follows hereafter.

SUMMARY OF THE INVENTION

This invention relates to an electrode for the excision of tissue from the cervix. The electrode, at one end, has a fine wire which can be rotated 360 degrees and which can be varied depending on the size of the cervix and the size of the lesion. This enables a single instrument to remove lesions, instead of using different sized instruments.

It is the primary object of the present invention to provide for an improved electrode for the excision of tissue.

Another object is to provide for such an electrode that is designed for use in the cervix and which allows different sized cervixes and different sized lesions to be treated with the same instrument.

These and other objects and advantages of the present invention will become apparent to readers from a consideration of the ensuing description and the accompanying drawings.

BRIEF DESCRIPTION OF THE DRAWINGS

FIG. 5A is a side view of the present invention in position at the cervix with a larger lesion.

FIG. 5B is a view of the lesion and the surrounding areas.

FIG. 5C is a view of the removed lesion.

FIG. 6A is a side view of the present invention in position at the cervix with an irregular shaped lesion.

FIG. 6B is a view of the lesion and the surrounding areas.

FIG. 6C is a view of the removed lesion.

FIG. 7 is a side view of another embodiment of the present invention.

FIG. 8 is a side view of the present invention in position inside the cervix.

FIG. 9 is a view of the lesion removed from the cervix.

DESCRIPTION OF THE PREFERRED EMBODIMENT

Figure 1:
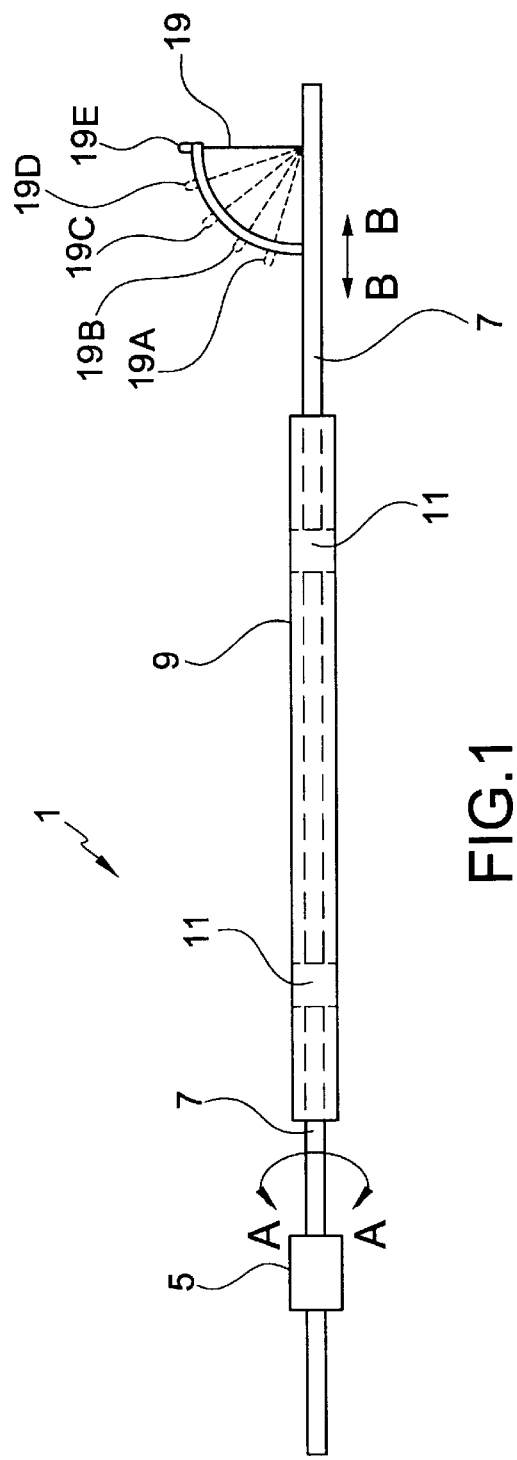
FIG. 1 is a side view of the present invention showing the electrode as it would appear in different angular positions.

FIG. 1 is a side view of the present invention showing the electrode 1 as the end 3, used for excision, would appear in different angular positions. At one end of electrode 1 is the handle 5. An inner tubular member or conduit 7 permits a energy to be transmitted through the conduit 7 to the distal end 3. Conduit 7 is substantially straight along the entire longitudinal axis. Electrode end 3 is to be inserted into the cervix of a patient and has a wire electrode that is used for excision. The rotatable handle 5 is fixed at, or near, the handle end of member 7. By rotating handle 5 the straight member 7 is also rotated as shown by the arrows AA in FIG. 1. In addition, the conduit 7 can be moved longitudinally with respect to member 9 as shown by the arrows BB in FIG. 1.

An outer tubular member or segment 9 surrounds a portion of the tubular member 7. Segment 9 extends along the length of member 7 and terminates adjacent end 3. Outer segment 9 is free to rotate relative to the inner member 7. In use, segment 9 is held by a user with one hand and handle 5 is held with the other hand. Appropriate conventional internal spacers 11, shown in dotted line format, are located along the length of segment 9 and have low friction surfaces. The spacers 11 are used to maintain the spacing between segment 9 and inner tubular member 7 while allowing for their relative rotation Not only is the conduit 7 rotatable relative to the segment 9, but it may be reciprocated longitudinally within the spacers 11. Appropriate marking may be provided along the length of member 7, adjacent 13, to inform the user of the angular rotation of conduit 7 relative to member 9 and the insertion depth of the conduit 7 relative to member 9.

A semicircular arm 15 is attached at end 3 and extends outwardly from conduit 7 in the same plane that contains the longitudinal axis of conduit 7. Extending from member 7 to arm 15 is a single wire electrode tip 19. The wire electrode tip 19 can be adjusted to any one of a plurality of different angular positions relative to the conduit 7. Five different possible angular positions labeled 19A, 19B, 19C, 19D and 19E are shown, however, it should be noted that more or fewer positions can be used with the present invention, as long as a plurality of positions are available. Electrode tip 19 is shown in solid line format in one position, 19E, with the other four position being in dotted line format. Typically, the angular variations between the electrode 19 and the conduit 7 would vary from about 90 degrees (starting at position 19E), to 75 degrees (19D), to 60 degrees(19C), to 45 degrees(19B), to 30 degrees for position 19A. Other angular relationships could, of course, be used and there could be more positions for the individual electrode 19 to be placed on the arm 15. It is the exposed free end or tip of wire electrode 19 that actually contacts the tissue for excision.

To adjust the electrode 19 to a different angular position, relative to the longitudinal axis of conduit 7, a user would initially move the wire electrode 19 into one of the positions (19A, 19B, 19C, 19D or 19E) where there is a slot or other holding mechanism for the specific angle desired on the arm 15. This positioning would be done before electrode end 3 is inserted into the patient. The wire for supplying power to electrode 19 extends through member 7 to a conventional power source (not shown) that can be used to generate and control the intensity of the energy to the tip 19. If desired, there could be several separate wire electrodes fixed to the arm 15 with a remote handle control being used to switch the tip to one of the desired angular positions.

Figure 2:
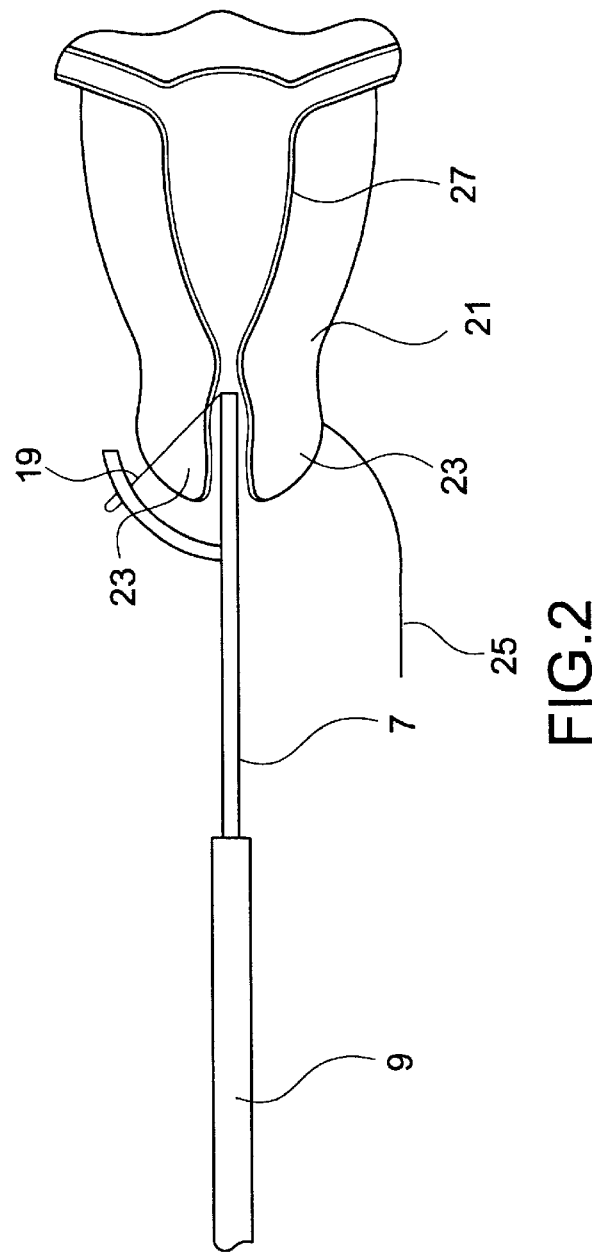
FIG. 2 is a schematic view showing the electrode of FIG. 1 being used in the cervix for the excision of tissue.

FIG. 2 is a schematic view showing the electrode 1 of FIG. 1 being used in the cervix 21 for the excision of a suspected abnormal tissue 23. In this example, the tip, shown in solid line format, is held in position 19E to provide for the excision. Since, conduit 7 can be rotated and moved in and out relative to member 9, many tissue samples on the surface on the cervix can be treated at just this one angular position. Providing for additional angular positions, by changing the angular position of the tip 19, provides for considerable flexibility in reaching suspected abnormal tissues of different configurations, sizes and positions within the cervix.

If desired, the same instrument could be used for excision of tissues from the vagina 25 (partially shown in FIG. 2), the fundus uteri 27 or any other part of the female reproduction tract that is accessible and suitable for excision by the electrode tip 19.

It should be noted that while the present invention has been described as using electrical energy supplied to the tip 19 through the conduit 7, other forms of energy such as, but not limited to, a laser could also be used.

Figure 3:
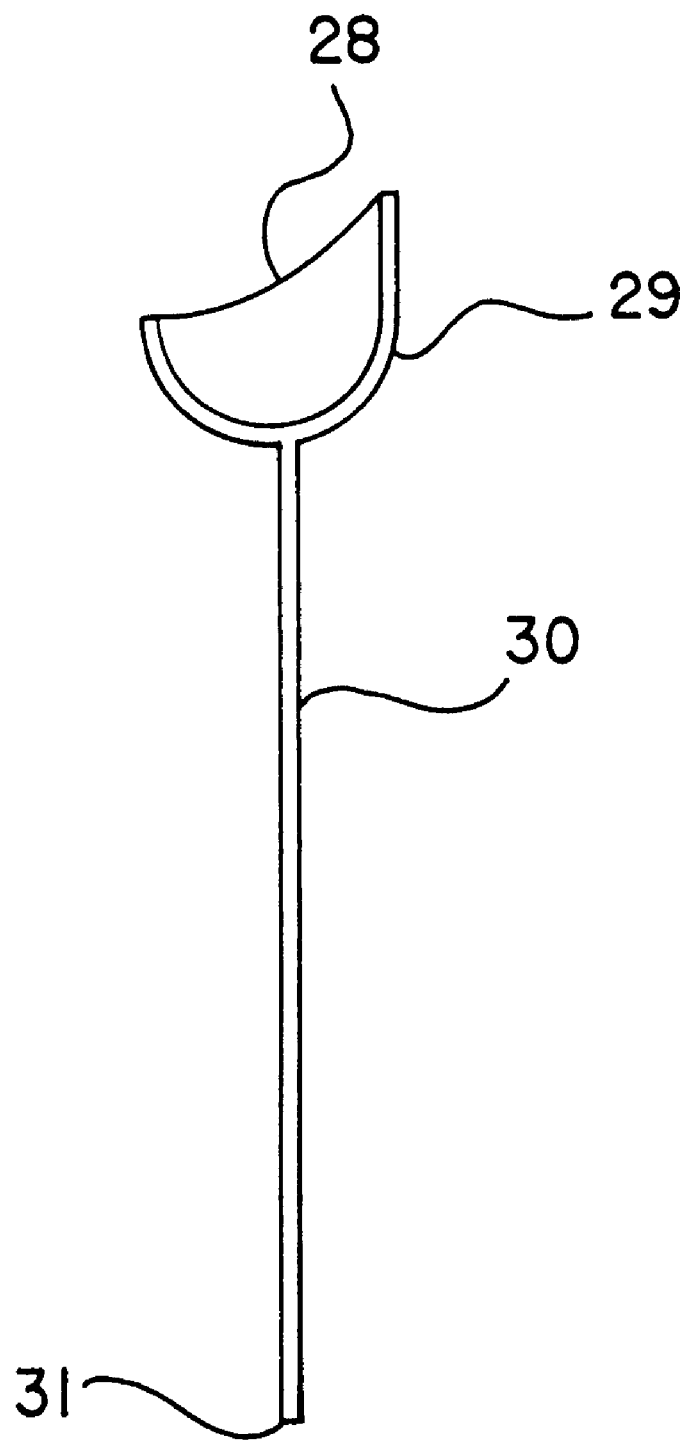
FIG. 3 is a side view of another embodiment of the present invention.

FIG. 3 shows an another embodiment of the present invention. The electrode has a handle 30 with a curved arm 29 at one end. The opposite end 31 of the arm 30 has an electrical wire (not show) connected thereto by any conventional means. As is conventional in the art, the wire will be electrically connected to an electrosurgical generator will supply the necessary electrical current to operate the electrode.

Attached to the curved arm 29 is a wire 28. Due to the curvature of the arm 29 the wire 28 assumes a concave shape. Also, since one of the ends of the curved arm 29 is shorter than the other end, the wire 28 is positioned at an angle with respect to the handle 30. Wires will run up the handle and be electrically connected to the ends of the wire 28. Since it is conventional to run electrical wires through medical instruments, further description is not necessary.

Due to the concave and angular structure of the wire 28, the electrode can be placed on the cervix and be rotated about the cervix in both circular and noncircular motions, using the handle 30. This will make excising cervical lesions easier. Also, the concave nature of the wire 28 allows the operator to adjust the width and depth of the excision. Therefore, one electrode can be used on various sized cervixes and different sizes and shapes of lesions.

Figure 4A:
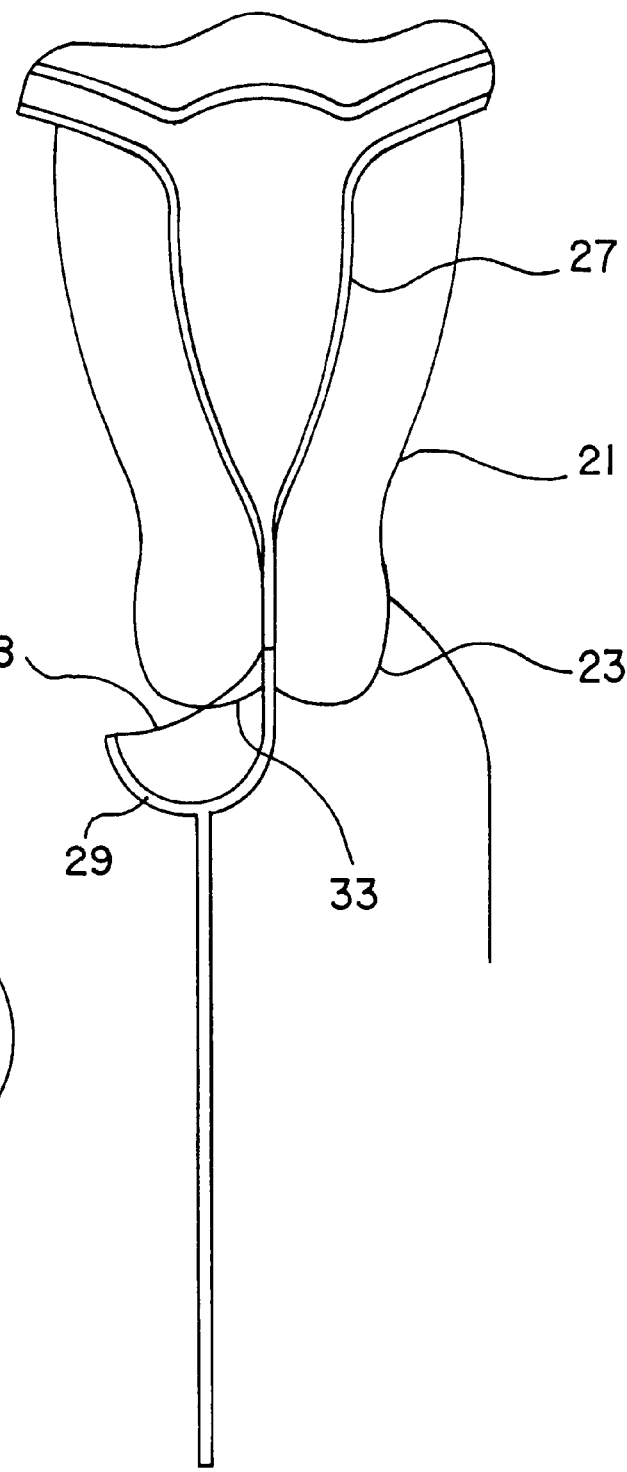
FIG. 4A is a side view of the present invention in position at the cervix.
Figure 4B:
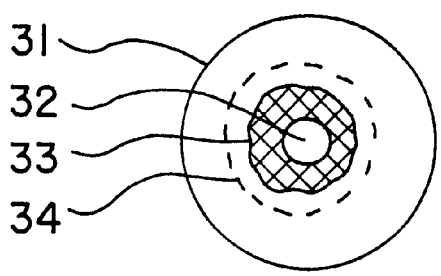
FIG. 4B is a view of the lesion and the surrounding areas.
Figure 4C:
FIG. 4C is a view of the removed lesion.

FIG. 4A shows the present invention being used on a small uterus with a small lesion 33. FIG. 4B shows the area being worked on by the electrode. 31 and 32 represent portions of the cervix, while 33 is the lesion, and 34 is the path of the cut made by the electrode. FIG. 4C shows the lesion 34 after it has been removed.

FIGS. 5A–5C are similar to FIGS. 4A–4C except the the uterus is larger and the lesion is larger. FIG. 5A shows the present invention being used on a larger uterus with a larger lesion 33'. FIG. 5B shows the area being worked on by the electrode. 31' and 32' represent portions of the cervix, while 33' is the lesion, and 34' is the path of the cut made by the electrode. FIG. 5C shows the lesion 34' after it has been removed. As shown by the arrow AA, the handle 30 has been pivoted toward the outside of the cervix in order to position the wire 28 in the proper position.

FIGS. 6A–6C are similar to FIGS. 4A–4C and FIGS. 5A–5C except the uterus is larger and the lesion is irregular. FIG. 6A shows the present invention being used on a larger lesion 33". FIG. 6B shows the area being worked on by the electrode. 31" and 32" represent portions of the cervix, while 33" is the lesion, and 34" is the path of the cut made by the electrode. FIG. 6C shows the lesion 34" after it has been removed.

FIGS. 7–9 show another embodiment of the present invention. In this embodiment the electrode has a handle 39 with a first end 38 and a second end 40. A wire, similar to the wire of the FIG. 3 device is attached to end 40 in the same manner and for the same reason. A wire 36 is attached adjacent end 38. The wire has two ends and they are attached so a space 37 extends between the wire 36 and a surface of the handle 39. FIG. 8 shows the electrode in position inside the cervix. In order to use the electrode the operator rotates the handle as shown by the arrows BB. As shown in FIG. 9 this operation will remove a circular plug 35.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. An electrode for the excision of tissue comprising:

a member having a length and a width, conduit means for transmitting energy capable of excision of tissue, said conduit means being positioned within said member, said conduit means having a tip at one end, a handle mounted near another end of said conduit means with respect to said member about a longitudinal axis of said member, angular positioning means mounted on said conduit means for adjusting said tip to different angular positions relative to said conduit means and, said angular positioning means is separate from said means for rotating said conduit means with respect to said member about a longitudinal axis of said member, wherein said angular positioning means comprises an arm fixedly mounted to said conduit means, said arm extends in an arc away from said conduit means, and wherein said tip extends from said conduit means to said arm, and said tip can be adjusted to a plurality of angular positions with respect to said conduit means, each of said angular positions holds said tip at a different angular position relative to the length of said conduit means.

2. The electrode as claimed in claim 1, wherein said conduit means is a hollow member, and means for transmitting energy extends through said conduit means, and said means for transmitting energy is connected to said tip.

3. The electrode as claimed in claim 1, wherein at least one of said angular positions holds said tip at an angle less then 90 degrees relative to said length of said conduit means.

4. The electrode as claimed in claim 1, wherein said conduit means has a longitudinal axis and said arms extends from said conduit means in a plane which includes said longitudinal axis.

5. The electrode as claimed in claim 1, wherein said conduit means moves longitudinally with respect to said member.

6. The electrode as claimed in claim 5, wherein spacer means are provided between said conduit means and said member for guiding said conduit means with respect to said member.

7. An electrode for excising diseased tissue, wherein said electrode comprises:

a handle, said handle having a first end and a second end, an arm secured to said first end of said handle, said arm having a first end and a second end, said first end of said arm being shorter than said second end of said arm, and an electrical wire, said electrical wire having a first end and a second end, said first end of said electrical wire being connected to a tip of said first end of said arm, and said second end of said electrical wire begin connected to a tip of said second end of said arm.

8. The electrode as claimed in claim 7, wherein said electrical wire has a concave shape.

9. The electrode as claimed in claim 7, wherein said arm is substantially U-shaped and has portions of different length.

\* \* \* \* \*